(12) United States Patent
Ke et al.

(10) Patent No.: US 6,284,773 B1
(45) Date of Patent: Sep. 4, 2001

(54) THERAPEUTIC COMBINATIONS COMPRISING A SELECTIVE ESTROGEN RECEPTOR MODULATOR AND PROSTAGLANDIN E2

(75) Inventors: HuaZhu Ke, Ledyard; David D. Thompson, Gales Ferry, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/314,371

(22) Filed: Jul. 14, 1999

Related U.S. Application Data

(60) Provisional application No. 60/089,468, filed on Jun. 16, 1998.

(51) Int. Cl.⁷ .................. A61K 31/445; A61K 31/19; A61K 31/557
(52) U.S. Cl. ........................ 514/317; 514/573
(58) Field of Search ....................... 514/317, 573

(56) References Cited

U.S. PATENT DOCUMENTS 5,552,412   9/1996   Cameron et al. ............... 514/317

FOREIGN PATENT DOCUMENTS

| 0911321 | 4/1999 | (EP) . |
| WO9716434 | 5/1997 | (WO) . |
| WO9731640 | 9/1997 | (WO) . |

OTHER PUBLICATIONS

Tang et a , J. Bone Mineral Research, 1992, 7, 1093–1104.

Shen et al., J. Clin. Invest, 1995, 96, 2231–38.

Scutt et al., Prostaglandins, *1995, 49*, pp. 383–395.

*Primary Examiner*—Theodore J. Criares
(74) *Attorney, Agent, or Firm*—Peter C. Richardson; Gregg C. Benson; Robert T. Ronau

(57) ABSTRACT

This invention is directed to pharmaceutical combination compositions and methods comprising (–)-cis-6-phenyl-5-(4-(2-pyrrolidin-1-yl-ethoxy)-phenyl)-5,6,7,8-tetrahydronaphthalene-2-ol or a pharmaceutically acceptable salt thereof and PGE2 or a pharmaceutically acceptable salt thereof, methods of using such compositions and kits containing such compositions. The compositions are useful for treating musculoskeletal frailty, including osteoporosis, osteoporotic fracture, low bone mass and frailty.

22 Claims, No Drawings

THERAPEUTIC COMBINATIONS COMPRISING A SELECTIVE ESTROGEN RECEPTOR MODULATOR AND PROSTAGLANDIN E2

CROSS-REFERENCE TO RELATED APPLICATIONS

This application claims the benefit of priority 35 U.S.C. §119(e) of copending U.S. Provisional Application No. 60/089,468, filed Jun. 16, 1998.

BACKGROUND OF THE INVENTION

This invention relates to a pharmaceutical combination of a selective estrogen receptor modulator (SERM) and PGE2 or a pharmaceutically acceptable salt thereof that stimulates bone formation, increases bone mass and enhances bone restoration effects of PGE2. The invention also relates to kits containing such combinations and the use of such combinations to treat musculoskeletal frailty, including osteoporosis, osteoporotic fracture, low bone mass, frailty and the like in mammals, including humans. In particular, this invention relates to a combination of (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof and PGE2 or a pharmaceutically acceptable salt thereof, kits containing such a combination and the use of such a combination to treat musculoskeletal frailty, including osteoporosis, osteoporotic fracture, low bone mass, frailty and the like in mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050.

Although both men and women are susceptible to musculoskeletal frailty, including osteoporosis, women are at greater risk of osteoporosis than men. Women experience a sharp acceleration of bone loss immediately following menopause. Other factors that increase bone loss leading to osteoporosis include smoking, alcohol abuse, a sedentary lifestyle and low calcium intake.

Estrogen is the agent of choice in preventing osteoporosis or post menopausal bone loss in women. In addition, Black, et al. in EP 0605193A1 report that estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer, endometrial cancer and possibly breast cancer, causing many women to either avoid this treatment or take the medication for only a short period of time. Although the risk of endometrial cancer is thought to be reduced by a concurrent use of a progesterone, there is still concern about possible increased risk of breast cancer with the use of estrogen. Recently suggested therapeutic regimens, which seek to lessen the cancer risk, such as administering combinations of progesterone and estrogen, cause the patient to experience unacceptable bleeding. Furthermore, combining progesterone with estrogen seems to blunt the serum cholesterol lowering effects of estrogen. The significant undesirable side effects associated with estrogen therapy support the need to develop alternative therapies for osteoporosis that have the desirable beneficial effect on serum LDL but do not cause undesirable side effects.

Recently, a number of selective estrogen receptor modulators have been proposed for treatment of osteoporosis. It has been reported (Osteoporosis Conference Scrip No. 1812/13 Apr. 16/20, 1993, p. 29) that raloxifene, 6-hydroxy-2-(4-hydroxyphenyl)-3-[4-(2-piperidinoethoxy)benzoyl]benzo[b]thiophene, mimics the favorable action of estrogen on bone and lipids but, unlike estrogen, has minimal uterine stimulatory effect. [Black, L. J. et al., Raloxifene (LY139481 Hcl) Prevents Bone Loss and Reduces Serum Cholesterol Without Causing Uterine Hypertrophy in Ovariectomized Rats, J. Clin. Invest., 1994, 93:63–69 and Delmas, P. D. et al., Effects of Raloxifene on Bone Mineral Density, Serum Cholesterol Concentration, and Uterine Endometrium in Postmenopausal Women, New England Journal of Medicine, 1997, 337:1641–1647].

Agents such as droloxifene, U.S. Pat. No. 5,254,595, prevent bone loss and thereby reduce the risk of fracture without estrogen's side effects. However, estrogen and estrogen agonists alone are only expected to reduce the fracture risk by about 50% leaving approximately 50% of osteopenic women still at risk for an osteoporotic fracture.

Commonly assigned U.S. Pat. No. 5,552,412, which is incorporated herein by reference, discloses SERM compounds of the formula

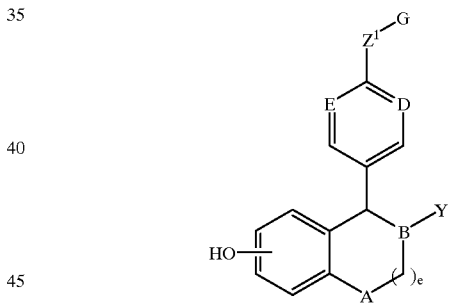

wherein the variables are defined as set forth therein. (−)-Cis-6-phenyl-5-(4-(2-pyrrolidin-1-yl-ethoxy)-phenyl)-5,6,7,8,-tetrahydronaphthalene-2-ol is an orally active, highly potent SERM which prevents bone loss, decreases total serum cholesterol, and does not have estrogen-like uterine stimulating effects in OVX rats.

PGE2 restores bone mass by stimulating both bone formation and bone resorption. However, in ovariectomized rat skeleton, PGE2 favors bone formation over bone resorption.

Tang et al., Restoring and Maintaining Bone in Osteogenic Female Rat Skeleton: I. Changes in Bone Mass and Structure, J. Bone Mineral Research 7 (9), p1093–1104, 1992 discloses data for the lose, restore and maintain (LRM) concept, a practical approach for reversing existing osteoporosis. The LRM concept uses anabolic agents to restore bone mass and architecture (+ phase) and then switches to an agent with the established ability to maintain bone mass, to keep the new bone (+/− phase). The rat study utilized $PGE_2$ and risedronate, a bisphosphonate, to show that most of the new cancellous and cortical bone induced by PGE$_2$ can be maintained for at least 60 days after discontinuing PGE$_2$ by administering risedronate.

Shen et al., Effects of Reciprocal Treatment with Estrogen and Estrogen plus Parathyroid Hormone on Bone Structure and Strength in Ovariectomized Rats, J. Clinical Investigation, 1995, 96:2331–2338 discloses data for the combination and/or sequential use of anti-resorptive agents and anabolic agents for the treatment of osteoporosis.

SUMMARY OF THE INVENTION

This invention is directed to a pharmaceutical composition comprising:

a. a first compound, said first compound being (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof; and b. a second compound, said second compound being PGE2 or a pharmaceutically acceptable salt thereof.

This invention is further directed to a pharmaceutical composition as recited in the immediately preceding paragraph additionally comprising a pharmaceutical carrier or diluent.

This invention is still further directed to a composition as set forth in either of the first two paragraphs of this summary wherein said first compound is (−)-cis-6-phenyl-5-(4-(2-pyrrolidin-1-yl-ethoxy)-phenyl)-5,6,7,8-tetrahydronaphthalene-2-ol D-tartrate and said second compound is PGE2 or a pharmaceutically acceptable salt thereof.

This invention is still further directed to a method, designated Method A, for treating a mammal suffering from musculoskeletal frailty comprising administering to said mammal a pharmaceutical composition as recited in any of the first three paragraphs of this summary.

A preferred method within Method A, designated Method B, is wherein said mammal is suffering from osteoporosis.

Another preferred method within Method A, designated Method C, is wherein said mammal is suffering from osteotomy, childhood idiopathic bone loss or bone loss associated with periodontitis.

This invention is still further directed to a method, designated Method A$^1$, for treating a mammal suffering from musculoskeletal frailty comprising administering to said mammal a. a first compound, said first compound being (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof; and b. a second compound, said second compound being PGE2 or a pharmaceutically acceptable salt thereof.

This invention is particularly directed to a method of Method A$^1$ wherein the first compound and the second compounds are administered substantially simultaneously.

This invention is also particularly directed to a method of Method A$^1$, hereinafter termed Method D, wherein the second compound is administered for a period of from about three months to about three years.

This invention is more particularly directed to a method of Method D followed by administration of the first compound for a period of from about three months to about three years without the administration of the second compound during the period of from about three months to about three years.

This invention is also more particularly directed to a method of Method D followed by administration of the first compound for a period greater than about three years without the administration of the second compound during the greater than about three year period.

This invention is also directed to a method, hereinafter termed Method E, for treating a mammal suffering from musculoskeletal frailty comprising administering to said mammal a therapeutically effective amount of a composition as recited in any of the first three paragraphs of this summary.

A preferred method within Method E is wherein bone healing following facial reconstruction, maxillary reconstruction or mandibular reconstruction is enhanced, vertebral synostosis is induced, long bone extension is enhanced, the healing rate of a bone graft or a long bone fracture is enhanced or prosthetic ingrowth is enhanced.

In all of the methods of this invention, it is preferred that the mammal is a human or a companion animal. The term "companion animal" refers to a household pet or other domesticated animal such as, but not limited to, cattle, sheep, ferrets, swine, horses, poultry, fish, rabbits, goats, dogs, cats and the like. Particularly preferred companion animals are dogs and cats.

In all of the methods of this invention, it is particularly preferred that the mammal is a human.

This invention is also directed to a kit comprising a treatment for a mammal suffering from musculoskeletal frailty comprising:

a. (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof and a pharmaceutically acceptable carrier or diluent in a first unit dosage form;

b. PGE2 or a pharmaceutically acceptable salt thereof and a pharmaceutically acceptable carrier or diluent in a second unit dosage form; and c. a container.

This invention is particularly directed to a kit as described in the immediately preceding paragraph wherein said first unit dosage form comprises (−)-cis-6-phenyl-5-(4-(2-pyrrolidin-1 -yl-ethoxy)-phenyl)-5,6,7,8-tetrahydronaphthalene-2-ol D-tartrate and said second compound is PGE2.

In all of the compositions, methods and kits of this invention, it is particularly preferred that the D-tartrate salt of (−)-cis-6-phenyl-5-(4-(2-pyrrolidin-1-yl-ethoxy)-phenyl)-5,6,7,8-tetrahydronaphthalene-2-ol is used.

The phrase "condition which presents with low bone mass" refers to a condition where the level of bone mass is below the age specific normal as defined in standards by the World Health Organization "Assessment of Fracture Risk and its Application to Screening for Postmenopausal Osteoporosis (1994), Report of a World Health Organization Study Group. World Health Organization Technical Series 843". Childhood idiopathic and primary osteoporosis are also included. Included in the treatment of osteoporosis is the prevention or attenuation of long term complications such as curvature of the spine, loss of height, prosthetic surgery, and prevention of prostate malfunctioning. Also included is increasing the bone fracture healing rate and enhancing the rate of successful bone grafts. Also included is periodontal disease and alveolar bone loss.

The phrase "condition which presents with low bone mass" also refers to a mammal known to have a significantly higher than average chance of developing such diseases as are described above including osteoporosis (e.g., postmenopausal women, men over the age of 60, and persons being treated with drugs known to cause osteoporosis as a side effect (such as glucocorticoid)).

Those skilled in the art will recognize that the term bone mass actually refers to bone mass per unit area which is sometimes (although not strictly correctly) referred to as bone mineral density.

The phrase "musculoskeletal frailty" refers to a condition wherein a subject has low bone mass and/or low muscle mass, and includes such diseases, disorders and conditions such as, but not limited to, conditions which present with low bone mass, osteoporosis, conditions which present with low muscle mass, osteotomy, childhood idiopathic bone loss, bone loss associated with periodontitis, bone healing following facial reconstruction, maxillary reconstruction, mandibular reconstruction and bone fracture. Further, musculoskeletal frailty encompasses such conditions as interfaces between newly attached prostheses and bone which require bone ingrowth.

The term "treating", "treat" or "treatment" as used herein includes curative, preventative (e.g., prophylactic) and palliative treatment.

The parenthetical negative or positive sign used herein in the nomenclature denotes the direction plane polarized light is rotated by the particular stereoisomer.

The compositions of this invention may include hydrates of the compounds used therein.

The expression "pharmaceutically acceptable salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl glucamine), benethamine (N-benzylphenethylamine), piperazine or tromethamine (2-amino-2-hydroxymethyl-1,3-propanediol).

The pharmaceutical compositions and methods of this invention result in higher magnitude bone mass gain than is achievable with the same doses of (−)- cis-6-phenyl-5-[4-(2-pyrrolidin-1 -yl-ethoxy)-phenyl]-5,6,7,8-tetrahydro-naphthalene-2-ol as described above alone or PGE2 or a pharmaceutically acceptable salt thereof as described above alone. Thus, combinations of the compounds of this invention increase bone mass and will decrease fracture rates to a greater extent than is achievable through use of either agent alone. This invention makes a significant contribution to the art by providing compositions and methods that increase and maintain bone mass resulting in prevention, retardation, and/or regression of osteoporosis and related bone disorders.

Other features and advantages will be apparent from the specification and claims which describe the invention.

DETAILED DESCRIPTION OF THE INVENTION

The first compound of this invention is (−)-cis-6-phenyl-5-[4-(2-pyrrolidin-1-yl-ethoxy)-phenyl]-5,6,7,8-tetrahydro-naphthalene-2-ol, or a pharmaceutically acceptable salt thereof, which has the structure of Formula I:

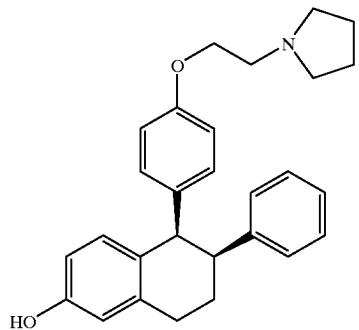

(−)-Cis-6-phenyl-5-[4-(2-pyrrolidin-1-yl-ethoxy)-phenyl]-5,6,7,8-tetrahydro-naphthalene-2-ol and the pharmaceutically acceptable salts thereof are prepared as described in commonly assigned U.S. Pat. No. 5,552,412, which is referenced above.

(−)-Cis-6-phenyl-5-[4-(2-pyrrolidin-1-yl-ethoxy)-phenyl]-5,6,7,8-tetrahydro-naphthalene-2-ol D-tartrate is prepared as set forth in the immediately preceding paragraph or, alternatively, as set forth in International Patent Application Publication Number WO97/16434, designating the United States and which is incorporated herein by reference.

The second compound of this invention is PGE2 (Sigma Chemical Company, 3050 Spruce Street, St. Louis, Mo., 63103) or a pharmaceutically acceptable salt thereof.

It will be recognized that PGE2 is acidic and will form a salt with a pharmaceutically acceptable cation. All such salts are within the scope of this invention and they can be prepared by conventional methods. Typical bases used to form such cationic salts are sodium hydroxide, sodium methoxide, sodium ethoxide, sodium hydride, potassium methoxide, magnesium hydroxide, calcium hydroxide, benzathine, choline, diethanolamine, piperazine and tromethamine. For example, the cationic salts can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds and pharmaceutically acceptable salts thereof used in the compositions and methods of this invention form hydrates or solvates such hydrates or solvates are also within the scope of the invention.

The pharmaceutical compositions and methods of this invention are all adapted to therapeutic use as agents that either activate bone turnover or prevent bone resorption or increase bone formation in mammals, particularly humans. Since these functions are closely related to the development of osteoporosis and bone related disorders, combinations of the compounds of this invention, by virtue of their action on bone, prevent, arrest, regress or reverse osteoporosis.

The utility of the compositions and methods of the present invention as medical agents in the treatment of musculoskeletal frailty (e.g., conditions which present with low bone mass or low muscle mass including osteoporosis) in mammals (e.g. humans) is demonstrated by the activity of the compounds of this invention in conventional assays as set forth in U.S. Pat. No. 5,552,412. Further evidence of the utility of the instant combination is set forth in Example One below. Such assays also provide a means whereby the activities of the compounds of this invention can be compared between themselves and with the activities of other known compounds. The results of these comparisons are useful for determining dosage levels in mammals, including humans, for the treatment of such diseases.

Administration of the compounds of this invention can be via any method which delivers a compound of the combination of this invention systemically and/or locally. These methods include oral routes, parenteral, intraduodenal routes, etc. Generally, the compounds of this invention are administered orally, but parenteral administration (e.g., intravenous, intramuscular, transcutaneous, subcutaneous or intramedullary) may be utilized, for example, where oral administration is inappropriate for the instant target or where the patient is unable to ingest the drug. The two different compounds of this invention can be co-administered simultaneously or sequentially in any order, or a single pharmaceutical composition comprising a first compound as described above and a second compound as described above in a pharmaceutically acceptable carrier or diluent can be administered.

In any event the amount and timing of compounds administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the activity (e.g., bone mass augmentation) that the physician considers appropriate for the individual patient. In considering the degree of activity desired, the physician must balance a variety of factors such as bone mass starting level, age of the patient, presence of preexisting disease, as well as presence of other diseases (e.g., cardiovascular). For example, the administration of (−)-cis-6-phenyl-5-(4-(2-pyrrolidin-1-yl-ethoxy)-phenyl)-5,6,7,8-tetrahydronaphthalen-2-ol can provide cardiovascular benefits, particularly for post-menopausal women. The following paragraphs provide preferred dosage ranges for the various components of this invention.

An effective dosage for (−)-cis-6-phenyl-5-[4-(2-pyrrolidin-1-yl-ethoxy)-phenyl]-5,6,7,8-tetrahydronaphthalen-2-ol is in the range of 0.0001 to 100 mg/kg/day, preferably 0.001 to 10 mg/kg/day.

An effective dosage for PGE2 is in the range of 0.0001 to 10 mg/kg/day, preferably 0.001 to 1.0 mg/kg/day.

Where the D-tartrate salt or other pharmaceutically acceptable salt of either of the above compounds is used in this invention, the skilled person will be able to calculate effective dosage amounts by calculating the molecular weight of the salt form and performing simple stoichiometric ratios. Where a pharmaceutically acceptable salt of PGE2 is used in this invention, the skilled person will be able to determine effective dosage amounts by calculating the molecular weight of the salt form and performing simple stoichiometric ratios.

The compounds of the present invention are generally administered in the form of a pharmaceutical composition comprising at least one of the compounds or pharmaceutically acceptable salts thereof of this invention together with a pharmaceutically acceptable carrier or diluent. Thus, the compounds and pharmaceutically acceptable salts thereof of this invention can be administered separately or together in any conventional oral, parenteral or transdermal dosage form. When administered separately, the administration of the other compound or pharmaceutically acceptable salt thereof of the invention follows.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds or pharmaceutically acceptable salts thereof of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of each active ingredient are known, or will be apparent in light of this disclosure, to those skilled in this art. For examples, see *Remington's Pharmaceutical Sciences*, Mack Publishing Company, Easton, Pa., 19th Edition (1990).

Pharmaceutical compositions according to the invention may contain 0.1%–95% of a combination of the compounds or pharmaceutically acceptable salts thereof of this invention, preferably 1%–70%. In any event, the composition or formulation to be administered will contain a quantity of the compounds or pharmaceutically acceptable salts thereof of the invention in an amount effective to treat the disease/condition of the subject being treated.

Since the present invention relates to treatment with a combination of the two active ingredients which may be administered separately, the invention also relates to combining separate pharmaceutical compositions in kit form. The kit includes two separate pharmaceutical compositions: (−)-cis-6phenyl-5-(4-(2-pyrrolidin-1-yl-ethoxy)-phenyl)-5,6,7,8-tetrahydronaphthalen-2-ol or a pharmaceutically acceptable salt thereof and PGE2 or a pharmaceutically acceptable salt thereof. The kit includes a container for containing the separate compositions such as a divided bottle or a divided foil packet, however, the separate compositions may also be contained within a single, undivided container.

Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a memory aid on a card insert, e.g., in the form of numbers next to the tablets or capsules whereby the numbers correspond with the days of the regimen which the tablets or capsules so specified should be ingested. Another example of such a memory aid is a calendar printed on the card e.g., as follows "First Week, Monday, Tuesday, . . . etc . . . Second Week, Monday, Tuesday, . . ." etc. Other variations of memory aids will be readily apparent. A "daily dose" can be a single tablet or capsule or several pills or capsules to be taken on a given day. Also a daily dose of SERM can consist of one tablet or capsule while a daily dose of PGE2 or a pharmaceutically acceptable salt thereof can consist of several tablets or capsules. The memory aid should reflect this.

In another specific embodiment of the invention a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

EXAMPLE ONE

S-D female rats were sham-operated (n=22) or ovariectomized (OVX, n=42) at 3 months of age. Five weeks post-surgery, OVX rats were treated with either vehicle, prostaglandin E2 (PGE2, 1 mg/kg/d (s.c.) in 20% ethanol/water), (−)-cis-6-phenyl-5-(4-(2-pyrrolidin-1-yl-ethoxy)-phenyl)-5,6,7,8,-tetrahydronaphthalene-2-ol (0.1 mg/kg/d (p.o.)), or combined PGE2 (1 mg/kg/d (s.c.)) and (−)-cis-6-phenyl-5-(4-(2-pyrrolidin-1-yl-ethoxy)-phenyl)-5,6,7,8,-tetrahydronaphthalene-2-ol (0.1 mg/kg/d (p.o.) for 5 weeks. Trabecular bone volume (TBV), percent labeling perimeter (L.Pm), osteoclast number per mm bone surface (Oc.N) were determined in proximal tibial metaphysis by standard static and dynamic histomorphometric techniques (Parfitt A. M. et al., Bone histomorphometry: Standardization of nomenclature, symbols, and units. J Bone Miner Res 2:595–610, 1997). Initial maximal load and stiffness of distal femoral metaphyseal trabecular bone were determined by indentation test for the rats sacrificed at week 10 according to the known method. (Meng, X. W. et al., Temporal expression of the anabolic action of PTH in cancellous bone of ovariectomized rats, J Bone Miner Res 11:421–429, 1996.)

Study Results and Discussion

OVX rats resulted in significant decrease in TBV (−33%) and significant increase in L.Pm (+48%) and Oc.N (+39%) at 5 weeks post-surgery as compared to sham controls. Continuous decrease in TBV was seen between 5 weeks and 10 weeks post-surgery in OVX rats (−20%). PGE2 at 1 mg/kg/d significantly increased TBV as compared to pre-treatment OVX controls (+22%) and OVX controls (+54%). However, TBV in OVX rats treated with PGE2 were still significantly lower than that in sham controls (−22%). (−)-Cis-6-phenyl-5-(4-(2-pyrrolidin-1-yl-ethoxy)-phenyl)-5,6,7,8,-tetrahydronaphthalene-2-ol treatment significantly decreased both L.Pm and Oc.N as compared to OVX controls. TBV in (−)-cis-6-phenyl-5-(4-(2-pyrrolidin-1-yl-ethoxy)-phenyl)-5,6,7,8,-tetrahydronaphthalene-2-ol treated rats was significantly higher than that in OVX controls and did not differ from the pre-treatment OVX controls, indicating that (−)-cis-6-phenyl-5-(4-(2-pyrrolidin-1-yl-ethoxy)-phenyl)-5,6,7,8,-tetrahydronaphthalene-2-ol prevented the further trabecular bone loss induced by OVX between 5 to 10 weeks post-surgery. Combination of PGE2 and (−)-cis-6-phenyl-5-(4-(2-pyrrolidin-1-yl-ethoxy)-phenyl)-5,6,7,8,-tetrahydronaphthalene-2-ol increased TBV to the level of sham controls, which was significantly higher than that in PGE2 or (−)-cis-6-phenyl-5-(4-(2-pyrrolidin-1-yl-ethoxy)-phenyl)-5,6,7,8,-tetrahydronaphthalene-2-ol alone treated groups. In the combination treated group, L.Pm significantly decreased by 15% and Oc. N decreased by 69% as compared to the PGE2 alone group, indicating that (−)-cis-6-phenyl-5-(4-(2-pyrrolidin-1-yl-ethoxy)-phenyl)-5,6,7,8,-tetrahydronaphthalene-2-ol inhibited more bone resorption than bone formation associated with OVX and PGE2; result in further increased bone mass in the OVX rats when compared to PGE2 alone. At week 10, initial maximal load and stiffness of distal femur decreased significantly in OVX rats as compared to sham controls (−66 and −56%, respectively). PGE2 or (−)-cis-6-phenyl-5-(4-(2-pyrrolidin-1-yl-ethoxy)-phenyl)-5,6,7,8,-tetrahydronaphthalene-2-ol alone significantly increased bone strength compared to OVX controls but was still significantly lower than the sham controls. However, when using combined treatment of PGE2 and (−)-cis-6-phenyl-5-(4-(2-pyrrolidin-1-yl-ethoxy)-phenyl)-5,6,7,8,-tetrahydronaphthalene-2-ol, bone strength was completely restored to the level of sham controls.

These data show that (−)-cis-6-phenyl-5-(4-(2-pyrrolidin-1-yl-ethoxy)-phenyl)-5,6,7,8,-tetrahydronaphthalene-2-ol inhibits bone resorption and bone turnover, prevents further bone loss and preserves bone strength in OVX rats. Furthermore (−)-cis-6-phenyl-5-(4-(2-pyrrolidin-1-yl-ethoxy)-phenyl)-5,6,7,8,-tetrahydronaphthalene-2-ol potentiates the bone restoration effects of PGE2 in established osteopenic, OVX rats. Thus, combination of (−)-cis-6-phenyl-5-(4-(2-pyrrolidin-1-yl-ethoxy)-phenyl)-5,6,7,8,-tetrahydronaphthalene-2-ol with PGE2 has utility in the treatment of postmenopausal bone loss.

It should be understood that the invention is not limited to the particular embodiments described herein, but that various changes and modifications may be made without departing from the spirit and scope of this novel concept as defined by the following claims.

What is claimed is:

1. A pharmaceutical composition comprising: in synergistic effective amounts
   a. a first compound, said first compound being (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof; and
   b. a second compound, said second compound being PGE2 or a pharmaceutically acceptable salt thereof.

2. A pharmaceutical composition of claim 1 additionally comprising a pharmaceutical carrier or diluent.

3. A pharmaceutical composition of claim 1 wherein said first compound is (−)-cis-6-phenyl-5-(4-(2-pyrrolidin-1-yl-ethoxy)-phenyl)-5,6,7,8-tetrahydronaphthalene-2-ol D-tartrate and said second compound is PGE2.

4. A method for treating a mammal suffering from musculoskeletal frailty comprising administering to said mammal a pharmaceutical composition of claim 1.

5. A method of claim 4 wherein said first compound is (−)-cis-6-phenyl-5-(4-(2-pyrrolidin-1-yl-ethoxy)-phenyl)-5,6,7,8-tetrahydronaphthalene-2-ol D-tartrate and said second compound is PGE2.

6. A method of claim 4 wherein said mammal is suffering from osteoporosis.

7. A method of claim 4 wherein said mammal is suffering from osteotomy, childhood idiopathic bone or bone loss associated with periodontitis.

8. The method of claim 4 wherein bone fracture, bone healing following facial reconstruction, maxillary reconstruction or mandibular reconstruction is treated, vertebral synostosis is induced or long bone extension is enhanced, the healing rate of a bone graft is enhanced or prosthetic ingrowth is enhanced.

9. The method of claim 8 wherein a bone fracture is treated in a human.

10. A method of claim 6 wherein osteoporosis is treated in a human.

11. A method for treating a mammal suffering from musculoskeletal frailty comprising administering to said mammal
   a. a first compound, said first compound being (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof; and
   b. a second compound, said second compound being PGE2 or a pharmaceutically acceptable salt thereof.

12. A method of claim 11 wherein the first compound and the second compound are administered substantially simultaneously.

13. A method of claim 11 wherein the second compound is administered for a period of from about three months to about three years.

14. A method of claim 13 followed by administration of the first compound for a period of from about three months to about three years without the administration of the second compound during the period of from about three months to about three years.

15. A method of claim 13 followed by administration of the first compound for a period greater than about three years without the administration of the second compound during the greater than about three year period.

16. A method of claim 11 wherein said mammal is suffering from osteoporosis.

17. A method of claim 16 wherein said mammal is a human.

18. A method of claim 11 wherein said mammal is suffering from osteotomy, childhood idiopathic bone loss or bone loss associated with periodontitis.

19. The method of claim 11 wherein bone fracture, bone healing following facial reconstruction, maxillary reconstruction or mandibular reconstruction is treated, vertebral synostosis is induced or long bone extension is enhanced, the healing rate of a bone graft is enhanced or prosthetic ingrowth is enhanced.

20. The method of claim 19 wherein a bone fracture is treated in a human.

21. A kit comprising:
   a. (−)-cis-6-phenyl-5-(4-(2-pyrrolidin-1-yl-ethoxy)-phenyl)-5,6,7,8-tetrahydronaphthalene-2-ol or a pharmaceutically acceptable salt thereof and a pharmaceutically acceptable carrier or diluent in a first unit dosage form;
   b. PGE2 or a pharmaceutically acceptable salt thereof and a pharmaceutically acceptable carrier or diluent in a second unit dosage form; and
   c. a container.

22. A kit of claim 21 wherein said first unit dosage form comprises (−)-cis-6-phenyl-5-(4-(2-pyrrolidin-1-yl-ethoxy)-phenyl)-5,6,7,8-tetrahydronaphthalene-2-ol D-tartrate and said second unit dosage form comprises PGE2.

* * * * *